United States Patent
Nørgaard

(10) Patent No.: US 9,986,939 B2
(45) Date of Patent: Jun. 5, 2018

(54) IN-SITU COMPENSATION OF ACOUSTIC MEASUREMENTS

(71) Applicant: Interacoustics A/S, Middelfart (DK)

(72) Inventor: Kren Rahbek Nørgaard, Middelfart (DK)

(73) Assignee: INTERACOUSTICS A/S, Middelfart (DK)

( * ) Notice: Subject to any disclaimer, the term of this patent is extended or adjusted under 35 U.S.C. 154(b) by 0 days. days.

(21) Appl. No.: 15/688,505

(22) Filed: Aug. 28, 2017

(65) Prior Publication Data

US 2018/0055421 A1    Mar. 1, 2018

(30) Foreign Application Priority Data

Aug. 26, 2016   (EP) .................... 16185824

(51) Int. Cl.
*A61B 5/12* (2006.01)
*A61B 5/00* (2006.01)

(52) U.S. Cl.
CPC ............. *A61B 5/12* (2013.01); *A61B 5/121* (2013.01); *A61B 5/7232* (2013.01); *G01N 2291/02491* (2013.01); *G01N 2291/02872* (2013.01)

(58) Field of Classification Search
None
See application file for complete search history.

(56) References Cited

U.S. PATENT DOCUMENTS 5,651,371 A    7/1997   Keefe
6,139,507 A   10/2000   Jeng

OTHER PUBLICATIONS

David Brass et al., "The effect of the evanescent wave upon acoustic measurements in the human ear canal", The Journal of the Acoustical Society of America, vol. 101, Apr. 1997, pp. 2164-2175.
Susan E. Voss et al., "Measurement of acoustic impedance and reflectance in the human ear canal", The Journal of the Acoustical Society of America, vol. 95, Jan. 1994, pp. 372-384.

*Primary Examiner* — Paul Huber
(74) *Attorney, Agent, or Firm* — Birch, Stewart, Kolasch & Birch, LLP

(57) ABSTRACT

The present disclosure relates to a method for estimating one or more compensation parameters from impedance measurements of an acoustic load. The method comprises a series of steps including providing a probe assembly measurement setup and the disclosure also relates to a system to perform impedance measurements. The compensation parameters are estimated through a minimization process, preferably minimizing an error estimate of a first real and second imaginary part of the reflectance. The resulting compensation parameters are used to restore causality of the reflectance and accordingly provide more accurate impedance measurements.

20 Claims, 7 Drawing Sheets

IN-SITU COMPENSATION OF ACOUSTIC MEASUREMENTS

FIELD

The present disclosure relates to a method to compensate for errors arising in acoustic impedance measures, such as acoustic impedance measures performed, e.g., within hearing diagnostics, acoustic mufflers, and/or musical acoustics applications. More particularly, the disclosure relates to an in-situ compensation method by which errors arising due to evanescent modes and an unknown characteristic impedance of an acoustic load are automatically estimated and compensated for. In more detail, the method accesses a reflectance measure based on an acoustic impedance measure to evaluate the errors arising in the impedance measure due to evanescent modes and causing inaccuracies in the reflectance measure of an acoustic load.

BACKGROUND

Measurements of acoustic impedance in, e.g., different acoustic loads are of interest in many branches of acoustics, including hearing diagnostics, acoustic muffler systems, and musical acoustics. These measurements are typically carried out with an impedance probe comprising an acoustic transducer, such as a receiver (generally also known as a speaker), delivering a stimulus (e.g., an input signal) to an applied acoustic load and an acoustic energy detector, such as a microphone of the probe, recording the reflected response. With a set of predetermined calibration parameters (such as the probe Thevenin calibration parameters) describing the source characteristics of the probe, the acoustic impedance of the acoustic load can be calculated from the probe response.

However, due to, e.g., physical differences in the coupling between the impedance probe and the acoustic load, errors causing artefacts in the impedance measurements may influence the impedance estimates calculated from the probe response. Artefacts causing errors in the impedance measurement includes, e.g., evanescent modes caused primarily by physical differences between the impedance probe and the acoustic load, for which the impedance should be measured by the probe.

Evanescent modes arise as a consequence of an acoustic volume velocity (i.e., stimuli) being injected into a waveguide across a limited part of an input plane thereof, exciting higher-order, non-propagating, evanescent modes. That is, the impedance probe used for impedance measurements of, e.g., an acoustic load necessarily has a smaller diameter than that of the acoustic load, to which the impedance probe is inserted. This results in evanescent modes being excited in the waveguide (i.e., the acoustic load for example being an ear canal) in addition to the propagating plane wave of the acoustic load, and consequently introduces errors in the impedance measured by the probe. Thus, the sought parameter, identified as the plane-wave impedance of the acoustic load, is often measured as a superposition of the actual plane-wave impedance and an unwanted non-plane-wave impedance of the acoustic load.

Calculating reflectance (i.e., reflection coefficient) from the measured impedance requires knowledge of the characteristic impedance of the acoustic load and the impedance measure, and the calculation of reflectance is therefore also affected by the errors caused by evanescent modes. Furthermore, the characteristic impedance of the acoustic load is closely related to the cross-sectional area of the acoustic load, which when performing measurements in, e.g., an ear canal is unknown. When investigating an acoustic load of unknown characteristic impedance, such as, e.g., the ear canal, the acoustic load is often assumed to have a specific, predefined characteristic impedance. This assumption introduces errors in the reflectance probe measurements caused by mismatches between the assumed and actual characteristic impedance experienced by the travelling wave down the length of an acoustic load coupled to the probe.

Therefore, for providing accurate measures of, e.g., reflectance and/or impedance, it is important that the characteristic impedance and/or the evanescent mode contribution are known. Research within the field of hearing diagnostics in acoustics has mainly focused on estimating the characteristic impedance in the ear canal, that is, several approaches regarding the estimation of characteristic impedance during in-situ measurements have been suggested. Some effort has also been put into compensating the contribution of evanescent modes in acoustic measurements without any success.

One known approach for approximating the effect of evanescent modes is to add to the impedance measure an acoustic mass as a compensation factor in series to the acoustic impedance. The acoustic mass is dependent on the diameter of the waveguide and the placement and size of acoustic input and output relative to each other. Relevant for evanescent mode compensation is thus to know and/or calculate an acoustic mass compensation factor related to the geometrical relationship between the impedance probe and the waveguide used for impedance measurements. However, this approach requires that geometrical parameters (such as the diameter) of the acoustic load in relation to the acoustic probe are known. This requirement is not always obtainable, when for example measuring acoustic impedance and sound pressure in human ear canals, where the ear canal may be considered as an acoustic load having an unknown characteristic impedance.

Other errors arising may include errors related to differences between the assumed characteristic impedance of an acoustic load in relation to the actual characteristic impedance experienced by a sound wave travelling through an acoustic load. Thus, the parameters causing errors in the impedance measurements of an acoustic load (e.g., a waveguide or a human ear canal), are dependent on knowing at least some physical characteristics (such as diameter and/or input/output relationship) of the acoustic load (e.g., a waveguide or ear canal) on which the characteristic impedance for the purpose of providing a reflectance measure should be measured. The physical characteristics of the acoustic load, for which the characteristic impedance should be estimated, are not always directly obtainable within acoustic applications.

Accordingly, no accurate method exists for determining the errors arising from evanescent modes in acoustic impedance measures. Thus, prior measurements have been affected by these errors. In addition, the prior art does not seem to take into account unknown parameters during in-situ measurements of an acoustic load (e.g., an ear canal), which would be of interest for, e.g., reflectance measurements.

Therefore, it is an object of the present disclosure to provide a method to compensate for errors arising in an impedance measure due to evanescent modes causing inaccuracies in a reflectance measure of an acoustic load having an unknown characteristic impedance, and an error arising in the reflectance measure due to the unknown characteristic impedance of the acoustic load. Furthermore, an object of the present invention is to use said compensation of the method to account for errors arising in, e.g., in-situ measurements of reflectance in the human ear canal, where the characteristic impedance of the acoustic load is unknown.

SUMMARY

This and further objects are in a first aspect achieved by a method to compensate for errors arising in impedance measures ($Z_m$) and subsequent reflectance measures of an acoustic load having an unknown characteristic impedance. The method substantially estimates one or more compensation parameters describing a first error arising in an impedance measure of an acoustic load due to evanescent modes causing inaccuracies in a reflectance measure (R) of said acoustic load, and describing a second error arising in the reflectance measure due to the acoustic load having an unknown characteristic impedance ($Z_0$).

The method comprises in more detail the steps of:
positioning a probe assembly in an acoustic load, the probe assembly comprising a speaker and a microphone, and said acoustic load having a first open end and a second at least partly closed end, wherein a distance between said first open end and said second at least partly closed end defines a length of the acoustic load;
generating from the speaker an acoustic output signal emitted into the acoustic load from the first open end and configured to propagate along the length of the acoustic load,
recording with the microphone of the acoustic probe an input signal caused by an incident part and a reflected part of the output signal propagating along said acoustic load, the incident part of the output signal comprising a plane-wave part and an evanescent-modes part, the method furthermore comprising the steps of
i) calculating an acoustic impedance ($Z_m$) based on a relation between the input signal and the output signal, wherein the acoustic impedance ($Z_m$) includes the first error due to the evanescent-modes part of the incident part, which first error are given as an approximation using an acoustic mass (L);
ii) setting a starting value ($Z_0'$) of the unknown characteristic impedance ($Z_0'$) of the acoustic load;
iii) calculating the reflectance measure (R) from a relationship between the measured acoustic impedance ($Z_m$) and the starting value ($Z_0'$) of the unknown characteristic impedance ($Z_0$);
iv) calculating a reflectance estimation error ($\varepsilon_R$) from a Hilbert transform of an imaginary part of said reflectance measure (R) subtracted from a real part of the reflectance measure (R) and added to a unit imaginary number (I) multiplied by an inverse Hilbert transform of the real part of the reflectance measure (R) subtracted from an imaginary part of said reflectance measure (R);
v) calculating a real part of the reflectance estimation error ($\varepsilon_R$) and an imaginary part of the reflectance estimation error ($\varepsilon_R$);
vi) adjusting the acoustic mass (L) iteratively until the imaginary part of the reflectance estimation error ($\varepsilon_R$) is minimized, thereby providing the first error arising in the reflectance measure due to the evanescent modes.

With this method, it is possible to compensate for an error caused by evanescent modes and introduced in an impedance measure, wherein the error introduces inaccuracies in the subsequent reflectance measure of the acoustic load and for an error arising in a subsequent reflectance measure due to an unknown characteristic impedance of the acoustic load. Accordingly, by using this method, different acoustic quantities such as impedance, reflectance, pressure, admittance measures, etc., may be estimated more accurately than previous suggested methods without knowing the physical properties of the acoustic load and/or the physical relation between the acoustic probe and the open end of the acoustic load under investigation. Accordingly, when for example measuring the impedance and reflectance of an ear canal, the geometry and physical properties of the ear canal in relation to the acoustic probe is unknown. When applying the method described herein, this "unknown" relationship, causing errors in the impedance and reflectance measure, may be compensated for by minimizing the errors introduced as explained in the methods steps above. As is apparent, the errors that are minimized are at least related to an unknown characteristic impedance (i.e., the second error) of the acoustic load (e.g., the ear canal) and a second error caused by evanescent modes being introduced into the impedance measure of an acoustic load.

Using the method according to the disclosure, it is possible to calculate a reflectance measure of an acoustic load, where the reflectance measure is not influenced by evanescent modes errors and errors caused by an unknown characteristic impedance. This enables a more accurate estimation of different acoustic properties, which may be found from the reflectance measure, than previously described methods within the literature. For example, within acoustics of human ear canals, the reflectance measure is often used to evaluate properties, such as the length of the ear canal, which, if affected by the errors described herein, becomes inaccurate. With the method described, such inaccuracies are avoided.

It should be noted, that the characteristic impedanc describes "a characteristic of said acoustic load", including the cross-sectional area of the acoustic load. Accordingly, when considering, e.g., a human ear canal, the cross-sectional error is substantially unknown and needs to be estimated, which said method does at least indirectly by compensating for an error resulting from a mismatch in characteristic impedance between a starting value for the characteristic impedance in the reflectance measure and the actual real characteristic impedance of the ear canal.

As previously elaborated on, the method furthermore takes into account an evanescent modes error arising due to "a coupling between the probe and the acoustic load" which describes the characteristics of the coupling between the probe and the acoustic load. That is, the errors related to the coupling between the probe and the acoustic load during in-situ measurements are mainly related to errors arising from evanescent modes.

With the term "probe assembly" should be understood an element at least including an acoustic probe. That is, the acoustic probe (also defined as an impedance probe) is an element comprising an acoustic source, such as a receiver (i.e., also denoted as a speaker), and an acoustic energy detector, such as a microphone. The acoustic probe may form part of a device, in which a processing unit is arranged so as to provide the impedance probe with an electrical input signal which subsequently allows the receiver of the impedance probe to emit a stimulus in the form of a signal. The acoustic probe may be attached to and/or form part of a handling tool, so as to form a "snout", "tip", and/or "earpiece" in an end of the handling tool, where the acoustic probe is intended to be inserted into the acoustic load, such as the ear canal of a human and/or animal.

The acoustic stimuli (also denoted an input signal) emitted into the acoustic load by the receiver of the acoustic probe may be any stimulus which is suitable for impedance measurements, such as clicks, chirps, sweeps, pure tones and/or noise.

Research on acoustical behaviour and properties of the setup used to measure impedances, such as providing an acoustic load to an acoustic probe, linking an external sound field to the acoustic load, such as an ear canal, show that a measure of reflectance provides a relation between the acoustic impedance and the characteristic impedance of an acoustic load. From investigations of the reflectance measure it has been realized that parameters related to the reflectance may aid in estimating a set of errors (i.e., said first error and said second error) needed to compensate for errors caused by evanescent modes and/or differences in actual and assumed characteristic impedance of the acoustic load, without having any prior knowledge about the physical dimensions of at least the acoustic load. Therefore, the reflectance measure may be used in the calculation step to provide an acoustic characterization of the acoustic load.

Accordingly, the method according to the first aspect takes advantage of the reflectance measure, such that in an embodiment, the calculation step comprises in more details the step of calculating the acoustic impedance ($Z_m$) of the acoustic load based on a relation between the input signal and the output signal of the speaker. The calculation of the acoustic impedance ($Z_m$) will include the first error due to evanescent modes, since the plane wave recorded at the microphone position in the acoustic load has a contribution from evanescent modes included therein. This of course leads to an error in the calculated impedance ($Z_m$). The first error caused by evanescent modes may be approximated using an acoustic mass (L), which should be considered as forming part of the acoustic impedance (Z), such that the actual impedance measure ($Z_m$) is given by:

$$Z_m = Z + i\omega L,$$

where L denotes the acoustic mass added to the calculated acoustic impedance due to evanescent modes. Accordingly, the method compensates for at least this first error by applying the steps according to claim 1.

In more detail, the method takes the advantage of using the reflectance measure given by $$\mathcal{R} = \frac{Z_m - Z_0}{Z_m + Z_0} \quad (1)$$

to estimate and compensate for the first errors introduced into the acoustic impedance ($Z_m$) and a second error, to be explained in the following introduced into the reflectance measure due to the unknown characteristic impedance ($Z_0$) of the acoustic load, where in equation (1) ($Z_m$) is the calculated acoustic impedance from the measured input signal by the acoustic probe and ($Z_0$) is the characteristic impedance of the acoustic load, such as a waveguide or ear canal. In many acoustic applications, the characteristic impedance of the acoustic load may be calculated from $$Z_0 = \frac{\rho c}{A} \quad (2)$$

where ρ is the density of the acoustic medium, c is the speed of sound and A is the cross-sectional area at the entrance of the acoustic load. However, as previously elaborated on, the physical parameters of the acoustic load, for example when investigating a human ear canal, are not always known, and the characteristic impedance cannot be calculated prior to the impedance measurements. According to the method described herein, the fact that the physical parameters are not known is not important, since the minimization of the errors related to the compensation parameters provides the optimum characteristic impedance and evanescent-modes compensation factor for restoring causality in the measurements. Accordingly, to compensate for the first and second errors introduced into the reflectance measure, the reflectance measure may be considered as $$\mathcal{R}_{est} = \frac{Z_m + i w L - Z_0'}{Z_m + i w L + Z_0'} \quad (3)$$

Where a starting value ($Z_0'$) is set for the of the unknown characteristic impedance ($Z_0$) of the acoustic load is set and the first error iωL related to the calculated acoustic impedance $Z_m$ due to evanescent modes, is added.

In the further step according to the method, a reflectance estimation error ($\varepsilon_R$) is calculated. This error is given by $$\varepsilon_{\mathcal{R}} = Re\,\mathcal{R} - \mathcal{H}_{(Im\,\mathcal{R})} + i[Im\,\mathcal{R} - \mathcal{H}^{-1}{(Re\,\mathcal{H})}],$$

where R is given as the reflectance and $\mathcal{H}$ is given as the denotation of a Hilbert transformation. Accordingly, as described in claim 1, the Hilbert transform of the Imaginary part of the reflectance (R) and the inverse Hilbert transform of the Real part of the reflectance (R) is used for determining the reflectance error estimate. With the use of the Hilbert transform it is possible to investigate the behaviour of the imaginary and real parts thereof. This allows an investigation of errors arising in the real and imaginary part, whereby an identification and accordingly as described herein a compensation of the introduced errors may be obtained by a minimization of the one or more error estimates related to said first acoustic impedance and said second characteristic impedance. The investigation of the errors mentioned herein may according to embodiments of the disclosure be performed by use of the Hilbert transform, which will become apparent throughout the description.

Accordingly, in a further step according to the method disclosed herein a real part of the reflectance estimation error ($\varepsilon_R$) and an imaginary part of the reflectance estimation error ($\varepsilon_R$) is calculated in accordance with $$Re\,\varepsilon_{\mathcal{R}} = Re\,\mathcal{R} - \mathcal{H}_{(Im\,\mathcal{R})},$$

$$Im\,\varepsilon_{\mathcal{R}} = Im\,\mathcal{R} - \mathcal{H}^{-1}{(Re\,\mathcal{R})}$$

R is the reflectance measure. Accordingly, it should be apparent that the real part of the estimation error, denoted Re $\varepsilon_R$ includes both the starting value $Z_0'$ for the characteristic impedance and the first error parameter iωL caused by evanescent modes arising in the input signal to the microphone. Similarly, the imaginary part of the reflectance measure, denoted Im $\varepsilon_R$, includes both the starting value $Z_0'$ for the characteristic impedance and the first error parameter iωL caused by evanescent modes arising in the input signal to the microphone. Thus, in the further step according to the method, the acoustic mass (L) is adjusted iteratively until the imaginary part of the reflectance estimation error Im $\varepsilon_R$ is minimized, thereby providing the first error arising in the reflectance measure.

Accordingly, in other words, in an embodiment, an initial compensation factor is added to the measured first acoustic impedance (i.e., the calculated acoustic impedance) prior to the step of calculating the one or more compensation parameters (i.e., parameters which may be considered as said first and second error).

In a further step of the method according to the disclosure, the starting value ($Z_0'$) of the unknown characteristic impedance may also be adjusted in order to compensate for an inaccurate starting value $Z_0'$ in relation to the actual true characteristic impedance ($Z_0$) of the acoustic load. Accordingly, said starting value ($Z_0'$) is similarly adjusted iteratively until the real part of the reflectance estimation error Re $\varepsilon_R$ is minimized, thereby determining the unknown characteristic impedance ($Z_0$) accounting for the second error arising in the reflectance measure due to the starting value ($Z_0'$) of the unknown characteristic impedance of the acoustic load.

Accordingly, when applying this method, it is possible to minimize the mentioned imaginary and real part of the reflectance estimation error Re $\varepsilon_\mathcal{R}$ in order to compensate for errors introduced into the impedance calculation and the subsequent reflectance calculation.

In other words, when providing initial compensation factors, i.e., the starting value ($Z_0'$) and (L), the minimization of the one or more error estimates is from a processing and calculation perspective optimized, while the errors are substantially compensated for in the reflectance measure.

For correctly compensating for the first error arising due to evanescent modes, the method step of adjusting the acoustic mass (L) iteratively, comprises the iterative steps of subtracting the acoustic mass (L) from the acoustic impedance measure ($Z_m$) and updating the reflectance measure and the imaginary part of the reflectance estimation error Im $\varepsilon_\mathcal{R}$ until the imaginary part of the reflectance measure is minimized. In this way an iterative update of the reflectance measure is achieved which results in a reflectance measure where the first error is compensated for.

It should be noted that adding an acoustic mass to a measured acoustic impedance is as such known in the prior art as means of approximating the effect of evanescent modes on acoustic impedance. However, according to the disclosure described herein, it has been realized, that the magnitude of the acoustic mass can be determined by means of the Hilbert transform, and by using the method described herein, the acoustic mass (L) may compensated for in an iterative process, rather than a manual adjustment of a reflectance measure. Accordingly, by the method described herein, the in-situ measurements account for the potential evanescent-modes errors introduced during in-situ measurements in, e.g., a human ear, where such errors also arise due to a geometrical mismatch between the acoustic load (e.g., human ear canal) and the acoustic probe. In this way, the method allows for even more accurate in-situ impedance measurements.

According to an embodiment, the initial compensation factor (i.e., the starting value for the acoustic mass (L)) is an estimate of an evanescent-modes error causing errors in the measured first acoustic impedance. Furthermore, the initial value for the characteristic impedance (i.e., the starting value ($Z_0'$) for the unknown characteristic impedance) may include an estimate of the diameter of the acoustic load to be used for impedance measurements, such as a human ear canal. For speeding up the convergence of the error estimates, the physical parameter, such as the diameter of the acoustic load, is chosen close to the actual diameter of the acoustic load. An appropriate initial diameter used for the characteristic impedance calculation and minimization could be in the range of 7.5 mm for an adult human ear canal and 4 mm for an infant ear canal. In essence, the starting value (i.e., the initial value) for the diameter should be chosen as an appropriate starting guess for the object of investigation.

With regards to the error estimates when calculating and estimating the compensation parameters, the inventor has found that the Hilbert transform may be used to compensate and substantially estimate the errors accounting for the inaccuracies introduced by evanescent modes and/or inaccuracies arising due to mismatches in characteristic impedance between the acoustic load and the assumed value by restoring causality in the reflectance measure and/or acoustic impedance. Accordingly, in the steps of adjusting the starting value ($Z_0'$) of the unknown characteristic impedance ($Z_0$) and the step adjusting the acoustic mass (L) accounts for a non-causality contained within the impedance measure due to the evanescent modes and the unknown characteristic impedance.

In other words, the Hilbert transform may be used to investigate the causality of a signal, and such investigations may be used in relation to the reflectance and/or acoustic impedance measures in order to calculate compensation factors (i.e., errors) related to at least evanescent modes and characteristic impedance of an acoustic load during in-situ measurements. In more detail, causality of a function is closely related to the dependency between the real and imaginary parts of the Fourier transform of that function. That is, any function can be separated into its even and odd components, where the Fourier transform of the even component results in the real part of the Fourier transform of the complete function, since the real part of the Fourier transform is the result of a comparison operation between the function and the even cosine. Additionally, the Fourier transform of the odd component is a comparison operation between the function and a sine, which results in the imaginary part of the Fourier transform of that function. If a function is causal, the even and odd parts are related by $$f_e(t) = f_o(t) sgn(t) \text{tm} \quad (4)$$

where $f_e(t)$ is the even part and $f_o(t)$ is the odd part of the function. Multiplying by the signum function, sgn(t), is equivalent to the Hilbert transformation when transformed to the Fourier domain. Accordingly, the causality of a signal can be investigated from the Hilbert transform providing a relationship between the real and imaginary parts of a signal spectrum, the Hilbert transform being given by:

$$R(\omega) = \frac{1}{\pi\omega} * X(\omega) \quad (5)$$

and similarly the inverse Hilbert transform given by $$X(\omega) = -\frac{1}{\pi\omega} * R(\omega) \quad (6)$$

where the asterisk denotes convolution and the integral is defined using the Cauchy principal value. $R(\omega)$ and $X(\omega)$ denotes the real and imaginary parts of the Fourier transform of the function, respectively. Thus, the Hilbert transform provides an efficient relationship between the imaginary part and the real part of the reflectance and/or acoustic impedance measure, which relationship may be used to iteratively estimate the compensation parameters needed to compensate for evanescent modes and errors introduced due to differences in characteristic impedance.

By restoring causality of the system when minimizing the real and imaginary part of the reflectance estimation error Im $\varepsilon_R$ using the Hilbert transformation, this allows for performing accurate in-situ measurements of an acoustic load having an unknown characteristic impedance.

In an embodiment, the first and second error estimates may be determined in two independent minimization processes. That is, the minimization of the real and imaginary parts of the reflectance estimation error may as already elaborated on be performed in two independent minimization processes. However, it could be possible to run the two processes in a single step, such that in an embodiment, the estimation further comprises the step of iteratively adjusting the starting value for $Z_0$ and the starting value for the acoustic mass (L) at the same time, whereby the minimization of the real part of the reflection estimation error and the imaginary part of the reflection estimation error Im $\varepsilon_R$ is performed at the same time.

In an embodiment, the method may include a further step of accounting for any discontinuities in the detected acoustic reflected signal spectrum. This may be done by adaptively adjusting the Nyquist frequency to restore continuity in the frequency domain.

It should be noted that the method may similarly work if looking directly at the measured impedance, whereby an impedance estimation error is calculated instead of said reflectance estimation error. Accordingly, the reflectance estimation error ($\varepsilon_R$) may be transformed into any other quantity representing said non-causality contained within said reflectance measure (R) due to said evanescent modes and said unknown characteristic impedance.

Impedance is inherently causal with a contribution in t=0 equal to the characteristic impedance, and since the evanescent modes only affect the imaginary part of impedance, it is possible to extract both parameters (i.e., the acoustic mass (L) and the unknown characteristic impedance ($Z_0$)) using the procedure method herein. This approach, however, is complicated by the non-smooth behaviour of the real and imaginary parts of acoustic impedance caused by resonances and the diverging nature of the acoustic impedance of occluded loads with $|Z| \to \infty$ as $\omega \to 0$. The real and imaginary parts of reflectance, on the other hand, are both smooth functions in most cases and typically $R \to 1$ as $\omega \to 0$ for occluded loads. Thus, reflectance is more suitable for this method than impedance.

In accordance with the embodiment described herein, it should be noted that the acoustic load may be any of a waveguide, an acoustic musical instrument, an acoustic muffler, a human ear canal or any other acoustical load for which an acoustic impedance is of interest. Accordingly, the method may be used to measure impedances, reflectance and/or sound pressure in any acoustic load of interest, where the physical properties, such as physical dimensions and evanescent-modes contribution are not known. Accordingly, the method provides for a compensation scheme, which may provide accurate and non-disturbed (i.e., plane-waves) impedance, reflectance, and sound-pressure measurements.

In a second aspect of the disclosure, an acoustic measurement system configured to output a reflectance measure (R) of an acoustic load is provided. The measurement system comprises a probe assembly configured to be arranged in an acoustic load, the acoustic load having a first open end and an at least partly closed second end, wherein the distance between the first open end and the at least partly closed second end defines a length of the acoustic load. The probe assembly furthermore comprising a speaker, a microphone, and a signal generating unit, wherein the signal generating unit is configured to generate from the speaker an output signal emitted into the acoustic load from the first open end, where the signal propagates along the length of the acoustic load. The microphone of the probe assembly is configured to record an input signal caused by an incident part and a reflected part of the output signal propagating along the acoustic load. In more detail, the measurement system comprises a calculation unit configured to perform the method steps according to the first aspect of the disclosure.

Furthermore, wherein the calculation unit takes as input at least the recorded input signal caused by the output signal being reflected from the at least partly closed end of the acoustic load for calculating the first acoustic impedance ($Z_m$) including an acoustic mass due to the evanescent modes according to step i) of claim 1, and a starting value of at least one of an acoustic mass (L) and/or said unknown characteristic impedance ($Z_0$) in accordance with the steps described in relation to the method described herein.

Accordingly, in an embodiment, the calculation unit may be configured to perform the method of the first aspect in order to compensate for evanescent modes and an unknown characteristic impedance by a minimization process.

In more detail, the calculation unit may output a reflectance measure (R) including the first error arising from the evanescent modes and the second error arising due to the unknown characteristic impedance ($Z_0$) and calculate a real part and an imaginary part of the reflectance estimation error (Im $\varepsilon_R$) according to the steps described in relation to the method described herein. In addition, the calculation unit is configured to output a corrected reflectance measure (R) upon performing adjustment steps of the starting values related to the acoustic mass (L) and the unknown characteristic impedance, whereby when a minimization has been achieved in the calculation, the output from the calculation unit may be a corrected reflectance estimation measure wherein the first error arising due to evanescent modes and the second error arising due to an unknown characteristic impedance of the acoustic load are compensated for.

BRIEF DESCRIPTION OF DRAWINGS

The aspects and embodiments of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features, and/or technical effect will be apparent from and elucidated with reference to the illustrations described hereinafter in which:

FIG. 12 shows a real time-domain reflectance measure of a waveguide according to FIGS. 8 and 10, where the first and second error has been compensated for.

DETAILED DESCRIPTION

The detailed description set forth below in connection with the appended drawings is intended as a description of various configurations. The detailed description includes specific details for the purpose of providing a thorough understanding of the various concepts. However, it will be apparent to those skilled in the art that these concepts may be practiced without these specific details. Several aspects of the methods, system, and related apparatus are described by various functional units, modules, components, circuits, steps, processes, algorithms, etc. (collectively referred to as "elements"). Depending upon particular application, design constraints, or other reasons, these elements may be implemented using electronic hardware, computer program, or any combination thereof.

Figure 1:
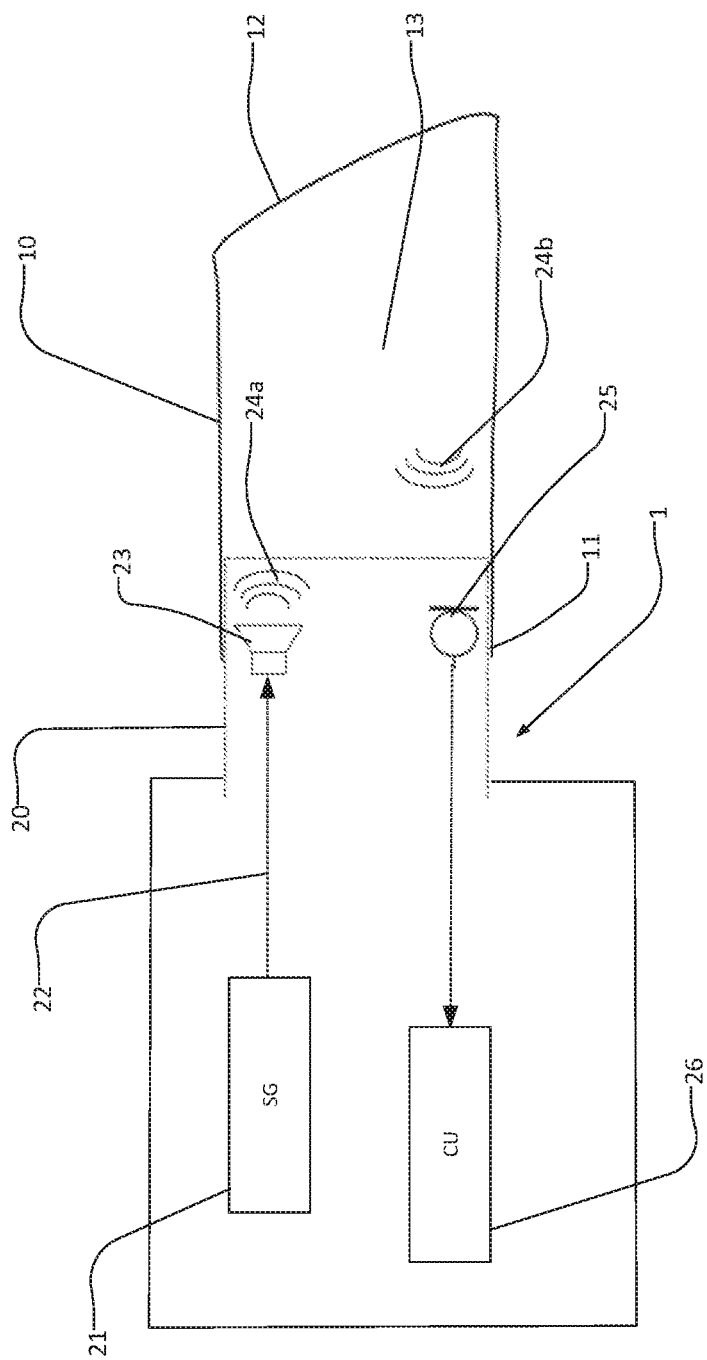
FIG. 1 schematically shows an acoustic load coupled to an acoustic probe according to embodiments of the disclosure.

Now referring to FIG. 1, an acoustic impedance measurement system 1 having an acoustic probe assembly 20 arranged in an acoustic load 10 (e.g., an ear canal) is schematically illustrated.

The acoustic measurement system is configured to measure an acoustic impedance of an acoustic load, such as the human ear canal and output a reflectance measure (R) of the acoustic load. The system generally comprises a probe assembly 20 configured to be positioned in an acoustic load 10. The acoustic load has a first open end 11 and a second at least partly closed end 12. The ends are separated at a distance from each other in order to form a channel in the acoustic load, the distance thus defining a length of the acoustic load. As an example, when using the measurement system for human ear measurements, the first open end 11 could be the ear canal opening and the second at least partly closed end 12 should be construed as the tympanic membrane. The probe assembly furthermore comprises a speaker and a microphone.

The system further comprises a signal-generating unit (SG) 21, generating from the speaker an output signal emitted into the acoustic load from the first open end and configured to propagate along the length of the acoustic load. The generating unit could also be considered so as to provide an electrical input signal 22 to an acoustic source (i.e., a speaker) 23 within the probe assembly 20. When the probe assembly is positioned in the first open end 11 of the acoustic load 10, the acoustic source (i.e., the speaker) 23 is configured to produce an acoustic stimulus 24a in response to the electrical input signal 22. The acoustic source 23 is illustrated as a receiver (also denoted a speaker), which is configured to emit sound into the channel 13 of the acoustic load. The channel 13 should be construed as an inner cavity of the acoustic load, which allows for sound to travel from one end thereof to a second end thereof. Thus, the receiver 23 is configured to emit a probe signal used by the measurement system to obtain an impedance measure.

Furthermore, the system comprises a signal-measuring unit (i.e., a microphone) configured to record an input signal caused by an incident part and a reflected part of the output signal propagating along the acoustic load. In other words, the microphone 25 arranged within the probe assembly 20 measures an acoustic reflected signal of the acoustic load. The acoustic reflected signal 24b is picked up by the microphone 25 and transmitted to a calculation unit (CU) 26. The calculation unit 26 is configured to compensate, based on the record, an input signal (also denoted the acoustic reflected signal) 24b, for one or more errors arising in the reflectance measure calculated by the calculation unit.

In more detail, the calculation unit 26 is configured to apply the method described in the previous sections of the disclosure. That is, the calculation unit is configured to perform the steps of:

i) calculating an acoustic impedance ($Z_m$) based on a relation between said input signal and said output signal, wherein said acoustic impedance ($Z_m$) includes said first error due to said evanescent-modes part of said incident part, which first error are given as an approximation using an acoustic mass (L);

ii) setting a starting value ($Z_0'$) of said unknown characteristic impedance ($Z_0$) of said acoustic load;

iii) calculating said reflectance measure (R) from a relationship between said measured acoustic impedance ($Z_m$) and said starting value ($Z_0'$) of said unknown characteristic impedance ($Z_0$);

iv) calculating a reflectance estimation error ($\varepsilon_R$) from a Hilbert transform of an imaginary part of said reflectance measure (R) subtracted from a real part of said reflectance measure (R) and added to a unit imaginary number (I) multiplied by an inverse Hilbert transform of said real part of said reflectance measure (R) subtracted from an imaginary part of said reflectance measure (R);

v) calculating a real part of said reflectance estimation error ($\varepsilon_R$) and an imaginary part of said reflectance estimation error ($\varepsilon_R$);

vi) adjusting said acoustic mass (L) iteratively until said imaginary part of said reflectance estimation error (Im $\varepsilon_R$) is minimized, thereby providing said first error arising in said reflectance measure due to said evanescent modes.

This substantially provides as output a corrected reflectance measure, in which reflectance measure the errors arising due to evanescent modes and the unknown characteristic impedance of the acoustic load has been accounted for.

In other words it could be said that the calculation unit is configured to calculate one or more compensation parameters $C_1(\omega)$, $C_2(\omega)$ from the calculation steps provided by the method. The one or more compensation parameters are substantially found by a minimization of one or more reflectance error estimates related to evanescent modes arising in the calculated acoustic impedance $Z_m$ and errors related to an unknown characteristic impedance $Z_0$ of the acoustic load. It should be noted that the method described herein is intended for use in in-situ acoustic measurements, where the characteristic impedance of the acoustic load is considered unknown. The method described herein therefore provides a solution to characterizing an acoustic load from e.g. the reflectance, without knowing the characteristic impedance of the acoustic load prior to the measurements.

In an embodiment, the calculation unit 26 takes as input at least the recorded input signal caused by the output signal being reflected from the at least partly closed end of the acoustic load for calculating the acoustic impedance ($Z_m$) including an acoustic mass due to the evanescent modes according to step i) of the method, and a starting value of at least one of an acoustic mass (L) and/or the unknown characteristic impedance ($Z_0$) according to step ii) the method.

In more detail, the measurement system is configured to perform the method described throughout the disclosure. The measurement system and more specifically the calculation unit 26 is therefore configured to calculate a reflectance error estimate, from the real and imaginary parts, which error estimate can be minimized in order to obtain a first error describing an evanescent mode contribution and a second error describing a contribution to the error in the reflectance arising from the unknown characteristic-impedance ($Z_0$). In other words a second error provided by the calculation unit, when the measurement system performs the method described herein, characterizes a compensation parameter $C_2$ related to a characteristic impedance mismatch between the acoustic load and the characteristic impedance. A first error estimate provided by the calculation unit of the measurement system characterizes a compensation parameter $C_1$ related to errors caused by evanescent modes resulting from the coupling between probe assembly and the acoustic load.

Specifically, the compensation factor $C_2$ should be considered as representative of the characteristic acoustic impedance $Z_c$ such that reflectance has the form $$R = \frac{Z_m + iwL - C_2}{Z_m + iwL + C_2} \quad (7)$$

where equation (7) is merely another way of describing equation (3). Accordingly, the compensation parameters mentioned herein should simply be construed as the acoustic mass (L) and the starting value for the characteristic impedance $Z_0'$, which as described are adjusted in said method in order to minimize the imaginary part of the reflectance estimation error Im $\varepsilon_R$ and the real part of the reflectance estimation error.

A parameter related to the characteristic impedance is the diameter of, e.g., an ear canal, which are used to calculate ear canal area needed for estimating the characteristic impendance. Accordingly, one parameter which is included in $C_2$ and which may be adjusted is the diameter of for example the ear canal of a hearing aid user, Another possibility could be to calculate an equivalent characteristic impedance including viscothermal losses.

As previously elaborated on, the compensation factor $C_1$ should be considered as a quantity that is either subtracted or added to the calculated impedance $Z_m$ such that $$Z = Z_m + C_1 \quad (8)$$

In the case of approximating evanescent modes using an acoustic mass, the factor takes the form $$C_1(\omega) = i\omega L \quad (9)$$

where L is the magnitude of the acoustic mass (positive or negative).

In other words, the measurement system comprises a data processing system, which has a processor adapted to execute a computer program for causing the processor to perform at least some (such as a majority or all) of the steps of the method described herein. A computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise. Accordingly, the measurement system is configured to perform the method to be described in more detail in the following.

Figure 2:
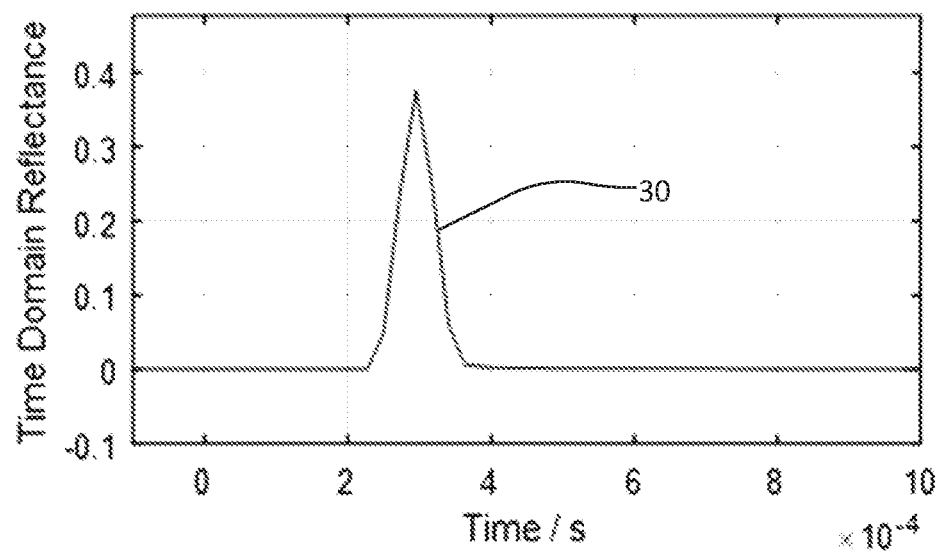
FIG. 2 shows an analytical time-domain reflectance measure of a uniform waveguide.

One of the interesting characteristics of acoustic measurements is the time-domain reflectance (TDR, also denoted the reflectance measure throughout the disclosure), which may be used to characterize an acoustic impedance and allows for an intuitive assessment of causality since non-zero samples below time zero are immediately visible. TDR is derived from the reflectance measure (R) using the inverse Fourier transform, as previously elaborated on. FIG. 2 illustrates an analytical time domain reflectance 30 used to investigate the properties of the method described herein. By analytical should be understood that the measurement is a representation of simulations performed in a computer program (such as MATLAB or other programming language) to illustrate the optimal behaviour of the time domain reflectance 30, that is, when no errors are introduced into the reflectance measure. In a real acoustic measurement application, several factors influence the time domain reflectance, causing errors in the acoustic measurements, as elaborated on in the previous sections. FIG. 2 shows that, in the case of an analytical plane wave impedance using a correct characteristic impedance and without any evanescent modes influencing the measure of the time-domain reflectance (TDR), the TDR is practically causal.

By using the method described herein, the behaviour of the time-domain reflectance as derived from the calculated impedance and an unknown characteristic impedance of an acoustic load, when introducing errors related to e.g. evanescent modes and characteristic impedance mismatch between the acoustic load and the acoustic probe has been investigated and an optimal solution for providing compensation for such errors has been found.

The method comprises the step of estimating a measure of reflectance, as given by equation 1. In the optimal measurement, represented as an analytical time-domain reflectance seen in FIG. 2, no compensation is apparently needed, since no irregularities caused by errors in calculation of the impedance $Z_m$ or from the subsequent calculation of reflectance due to an unknown acoustic load are introduced. Accordingly, in FIG. 1 it should be understood that the characteristic impedance of the acoustic load under consideration has been known, why there are no errors introduced into the reflectance measure (R). It is clear from FIG. 2 that the analytical TDR is practically causal, since the real part and the imaginary part 31, 32 of the reflectance estimation error is substantially centred around zero. However, to explain, how the method may compensate for potential errors introduced in the reflectance measure (R) and thus also in impedance measures during in-situ measurements, the analytical investigations of the time-domain reflectance (TDR) preceding this application will be elaborated on.

Figure 3:
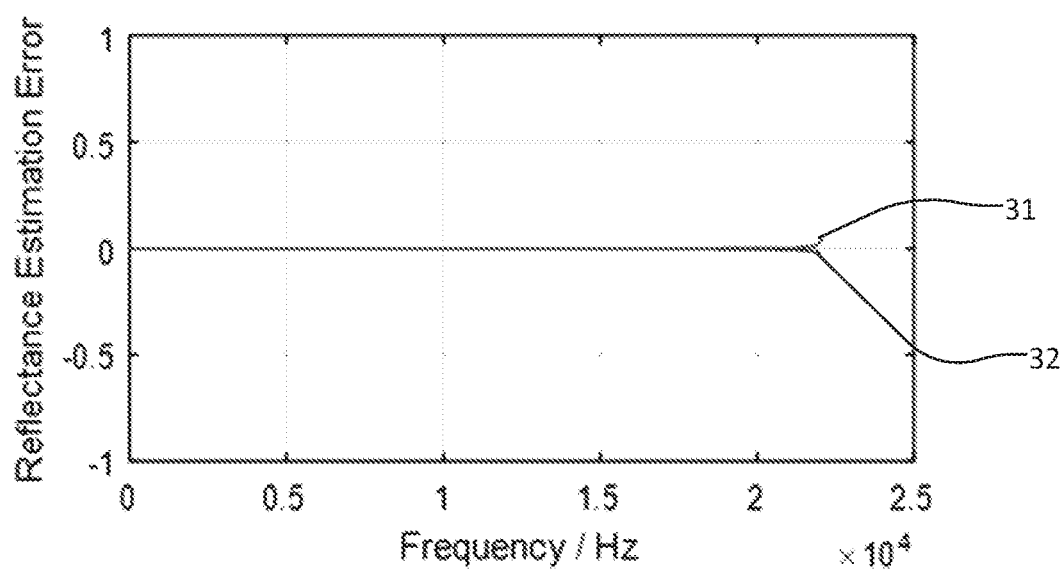
FIG. 3 shows an analytical representation of the reflectance estimation error of the optimal reflectance measure in FIG. 2.

When using the method according to the disclosure, the relationship between a first real and second imaginary part of the reflectance is provided by using a Hilbert transform. As previously elaborated on, the Hilbert transform describes a relationship between the real and imaginary part, from which relationship causality may be investigated and restored if the reflectance spectrum is non-causal. Accordingly, by looking at (i.e., calculating) the reflectance estimation error ($\varepsilon_R$) and subsequently calculating the imaginary part (Im $\varepsilon_R$) of the reflectance estimation error and the real part (Re $\varepsilon_R$) of the reflectance estimation error, it is possible to get an overview of the causality characteristics of a signal (here the TDR). This is shown in FIG. 3, where the real part of the reflectance estimation error (Re $\varepsilon_R$) 31 and the imaginary part of the reflectance estimation error (Im $\varepsilon_R$) 32 according to the Reflectance measure (R) of FIG. 2 is illustrated. As can be seen from FIG. 3, the error estimates are substantially zero for the optimal analytical situation, and the TDR of FIG. 2 may from FIG. 3 be confirmed to be causal.

Accordingly, the method is aiming at achieving an optimal reflectance estimation error ($\varepsilon_R$) resulting in an imaginary part thereof (Im $\varepsilon_R$) and an real part thereof (Re $\varepsilon_R$), which are substantially centred around zero. This provides more accurate acoustic measurements of impedance, pressure and reflectance.

Therefore, further investigations on a method to restore causality has been performed by introducing at least two different errors into the analytical TDR measure of FIG. 2. When performing in-situ acoustic measurements, such as in an ear canal of a user, a first factor introducing a first error into the TDR is dependent on the characteristic impedance mismatch between the acoustic probe and the acoustic load, that is a second error arises from not knowing the characteristic impedance $Z_0$ of the acoustic load under investigation, and a second factor introducing a first error is related to evanescent modes. Therefore, to provide a method accounting for such errors, such first and second errors have been introduced into the analytical TDR of FIG. 2 in the following figures.

For the sake of simplicity, the effect of the two errors on the reflectance measure (R) and the individual compensation thereof will be explained independently in the following sections. However, it should be noted that the method provides the option of compensating both errors in a combined step or in two separate steps.

Figure 4:
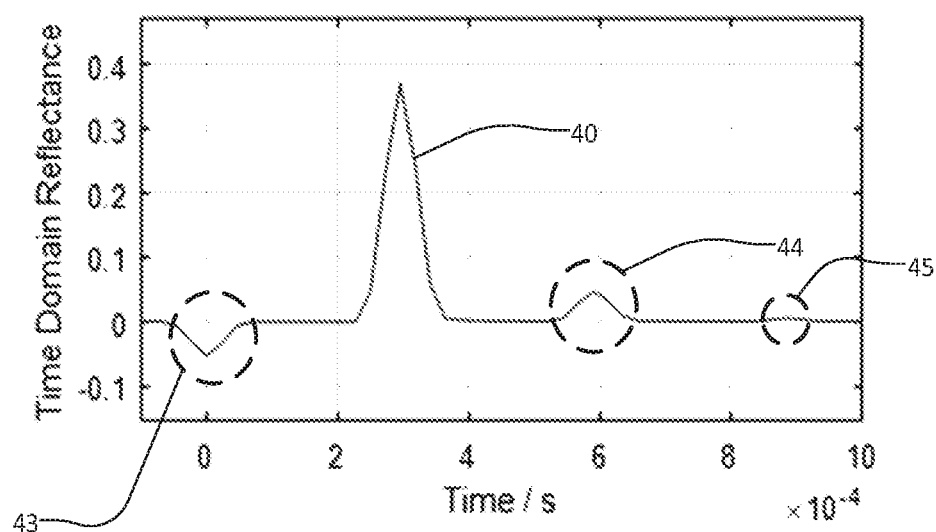
FIG. 4 shows an analytical time-domain reflectance measure, where a second error is introduced.

Setting out with explaining a second error, which may be related to a characteristic-impedance mismatch reference is made to FIG. 4. FIG. 4 shows the behaviour of the analytical TDR, when the second error has been introduced into the TDR of FIG. 2. In FIG. 4, the TDR is derived from the analytical impedance (i.e., a measured impedance of an analytical acoustic load) of a waveguide of radius a=4 mm and L=5 cm, but with the characteristic impedance $Z_0$ derived from a waveguide of a=3.5 mm. As can be seen from FIG. 4, the TDR signal 40 is substantially irregular in the areas circled and denoted 43, 44 and 45. Accordingly, when performing measurements in an acoustic load, such as the waveguide, a mismatch is present between the characteristic impedance $Z_0$ of the acoustic load and the probe, which cause the irregularities 43, 44 and 45 illustrated in FIG. 4. If the characteristic impedance $Z_0$ of the acoustic load is not known, which is often the case for in-situ acoustic measurements (especially ear-canal in-situ measurements), a compensation parameter $C_2$, also denoted a second error, taking into account this unknown characteristic impedance is needed to remove the irregularities in the TDR. The errors are similarly illustrated in FIG. 5 as a shift in the real part of the reflectance estimation error 41 towards minus.

In order to account for such an irregular behaviour in the TDR, the method according to embodiments of the disclosure suggest to use the Hilbert transform to calculate the reflectance estimation error and subsequently calculating the real part of the reflectance estimation error Re $\varepsilon_R$ and the imaginary part of the reflectance estimation error Im $\varepsilon_R$, which in case of the errors arising due to the unknown characteristic impedance $Z_0$ are compensated for by minimizing the real part of the reflectance estimation error Re $\varepsilon_R$, hereby determining the unknown characteristic impedance ($Z_0$) accounting for the second error arising in the reflectance measure due to the starting value ($Z_0'$) of the unknown characteristic impedance ($Z_0$) of the acoustic load.

In more detail, the method establishes a relationship between the first real and second imaginary part from a Hilbert transform, as previously elaborated on. From such relationship, a calculation of one or more error estimates of the real part of said measure of reflectance from the imaginary part of the measure of reflectance and/or of the imaginary part of the measure of reflectance from the real part of the measure of reflectance using said Hilbert transform is performed, which results in the error estimates, e.g., illustrated in FIGS. 3 and 5. As is seen from FIGS. 3 and 5, when comparing these figures, it is clear that the analytical TDR 40 of FIG. 4, introducing an error is non-causal and that the error introduced influences the real part of the reflectance error estimate Re $\varepsilon_R$.

To restore causality in the TDR signal 40, the error introduced into the TDR 40 is minimized by minimizing the real part of the reflectance estimation error as previously described. Particularly, for the second error, it is clear from FIG. 5, that the minimization of the error in the real part is especially important in order to restore causality and achieve more accurate measurements, when seen in relation to a characteristic impedance mismatch between the acoustic probe and the acoustic load. The minimization of the real part of the reflectance estimation error Re $\varepsilon_R$ shifts the real part thereof back towards zero.

Figure 6:
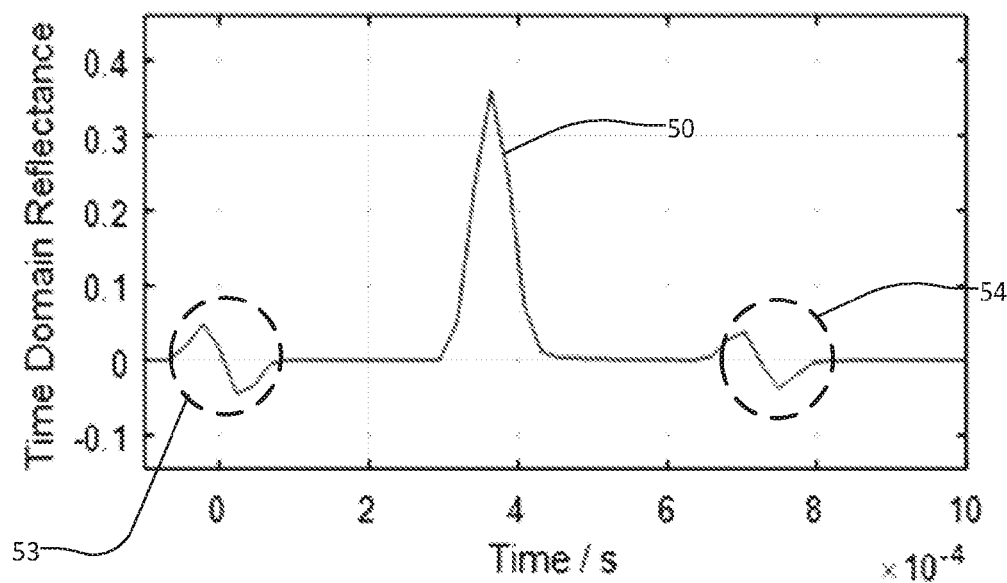
FIG. 6 shows an analytical time-domain reflectance, where a first error is introduced.
Figure 7:
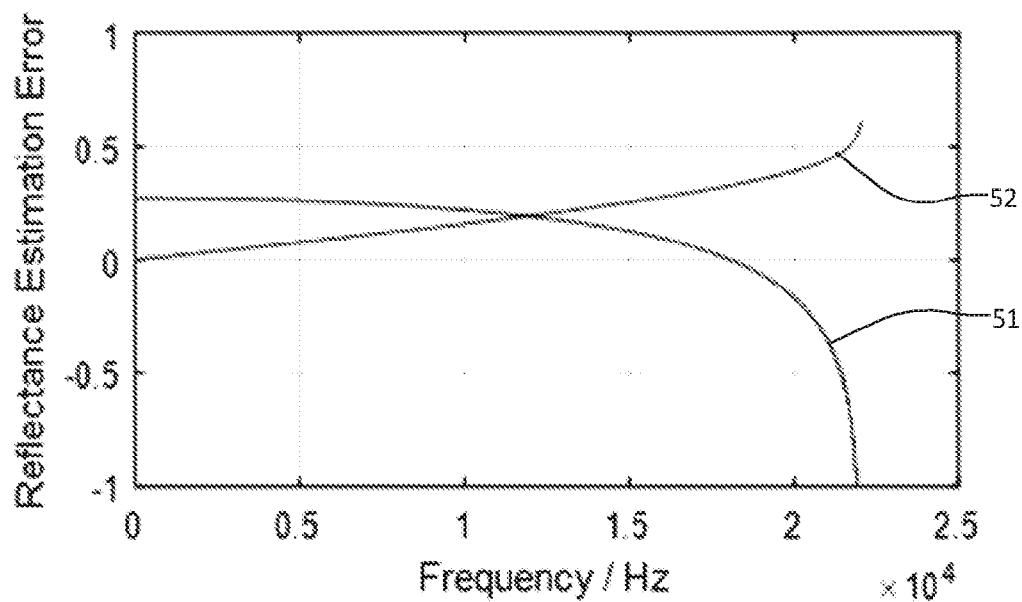
FIG. 7 shows an analytical representation of the reflectance estimation error, where the first error of FIG. 6 is illustrated.

Turning now to the first error, which may be related to errors arising due to a geometric mismatch between the acoustic probe and the acoustic load causing evanescent modes, reference is made to FIGS. 6 and 7. FIG. 6 show the behaviour of the analytical TDR 50, when the second error has been introduced into the analytical TDR of FIG. 2. The TDR 50 of FIG. 6 is derived from the analytical impedance of a waveguide with a=4 mm and L=5 cm, but with an evanescent-modes factor simulated by an acoustic mass of L=130. As can be seen from FIG. 6, the TDR signal 50 is substantially irregular in the areas circled and denoted 53 and 54. Furthermore, as seen from FIG. 7, the real part 51 and imaginary part 52 of the reflectance estimation error clearly show a non-causal behaviour of the TDR. Accordingly, when performing measurements in an acoustic load, a geometric mismatch is present between the openings of the acoustic load in comparison to the acoustic probe assembly, which substantially causes the irregularities 53, 54 illustrated in FIG. 6. This geometrical mismatch is generally known to cause evanescent modes. Such evanescent modes also arise when the acoustic probe is inserted into an acoustic load during in-situ measurements, such as when inserted into, e.g., an ear canal of a human, and therefore also need to be compensated for during in-situ impedance measurements. In a similar way as previously described, the error introduced due to evanescent modes may be compensated for by using the method described herein. That is, the evanescent-modes contribution is compensated by calculating the reflectance estimation error ($\varepsilon_R$) from a Hilbert transform of an imaginary part of the reflectance measure (R) subtracted from a real part of the reflectance measure (R) and added to a unit imaginary number (I) multiplied by an inverse Hilbert transform of the real part of said reflectance measure (R) subtracted from an imaginary part of the reflectance measure (R); and subsequently calculating a real part of the reflectance estimation error (Re $\varepsilon_R$) and an imaginary part of the reflectance estimation error ($\varepsilon_R$); wherein in a final step, the acoustic mass (L) is adjusted iteratively until the imaginary part of the reflectance estimation error ($\varepsilon_R$) is minimized, thereby providing the first error arising in the reflectance measure due to the evanescent modes.

According to the method, it is therefore achieved that evanescent modes introduced during in-situ measurements are compensated for.

Similarly, as with the second error, the method establishes a relationship between the first real 51 and second imaginary part 52 from a Hilbert transform, as previously elaborated on. From such relationship, a calculation of one or more error estimates of the real part of said measure of reflectance from the imaginary part of the measure of reflectance and/or of the imaginary part of the measure of reflectance from the real part of the measure of reflectance using the Hilbert transform is performed, which result in the reflectance estimation errors, e.g., illustrated in FIG. 7 for the first error. As is seen from FIGS. 3 and 7, when comparing these figures, it is clear that the analytical TDR 50 of FIG. 6, introducing a first error is non-causal and that the error introduced influences both the real 51 and imaginary part 52 of the reflectance error estimates. However, it is seen from FIG. 7, that the error estimate of the imaginary part seems to exhibit a frequency proportional relationship, whereas the real part is less predictable.

In an embodiment according to the disclosure, the method furthermore includes an initial compensation factor added to the impedance $Z_m$, in order to provide an initial guess for the influence of the evanescent modes. In effect of adding such initial guess to the calculation of the error estimates for the second error, a faster convergence is achieved. The initial guess should be construed as the starting value for adjusting the acoustic mass (L).

Figure 5:
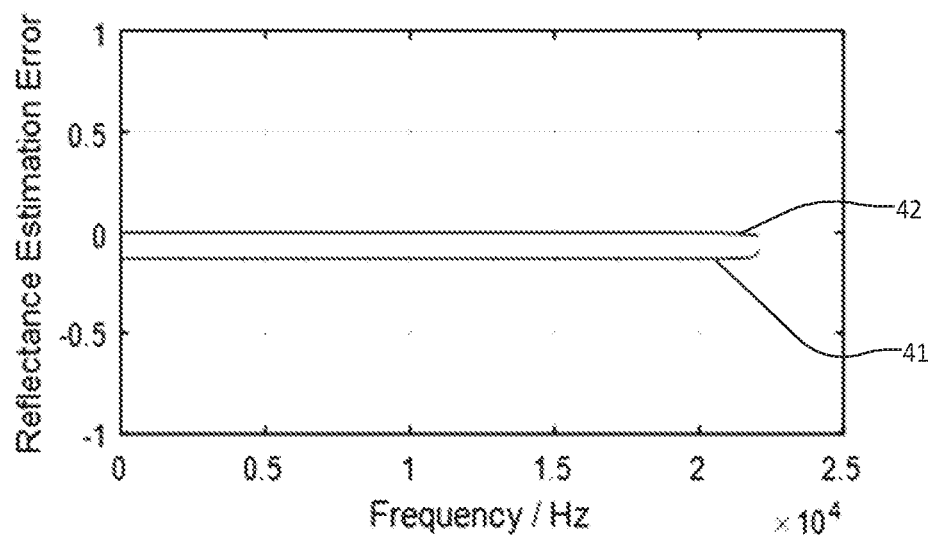
FIG. 5 shows an analytical representation of the reflectance estimation error where the second error of FIG. 4 is illustrated.

From investigations of the behaviour according to FIG. 7 and when looking at the error estimates of FIG. 5, related to the second error, it is clear that the second error only influences the real part of the reflectance estimation error Re $\varepsilon_R$, whereas the first error influences both the real part of the reflectance estimation error and the imaginary part of the reflectance estimation error Im $\varepsilon_R$. To summarize, this means that the characteristic impedance mismatch mainly introduces errors in the real part of the reflectance error estimates, and the geometrical mismatch (e.g., causing evanescent modes) mainly introduces errors in the imaginary part of the reflectance error estimates Im $\varepsilon_R$. Thus, in order to achieve accurate acoustic impedance measurements and reflectance measurements, both errors should preferably be compensated for, so that causality in the reflectance is restored.

To show the efficiency of the method in relation to a real measurement application, the method will be described when used in relation to measurements in a real waveguide, such as an acoustic load. Thus, reference is now made to FIGS. 8 to 13, showing the same investigations as described in relation to the analytical investigation of FIGS. 2 to 7.

Figure 8:
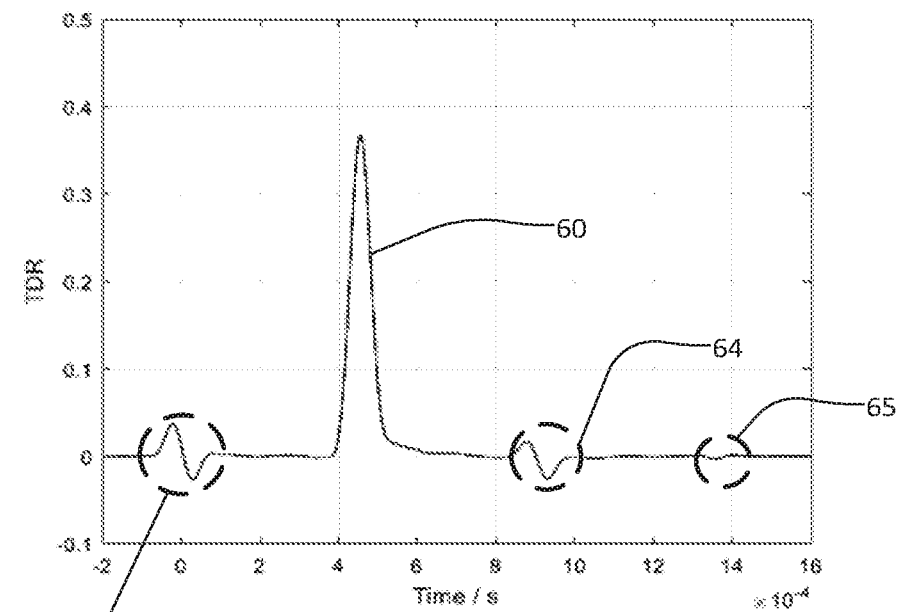
FIG. 8 shows a real time-domain reflectance measure of a waveguide according to an embodiment of the disclosure where a first error is present.

Initially referring to FIG. 8, the TDR 60 from a measurement of an 8×Ø0.8 cm waveguide, such as an acoustic impedance, without any evanescent mode compensation and using the correct known characteristic impedance is shown.

Figure 9:
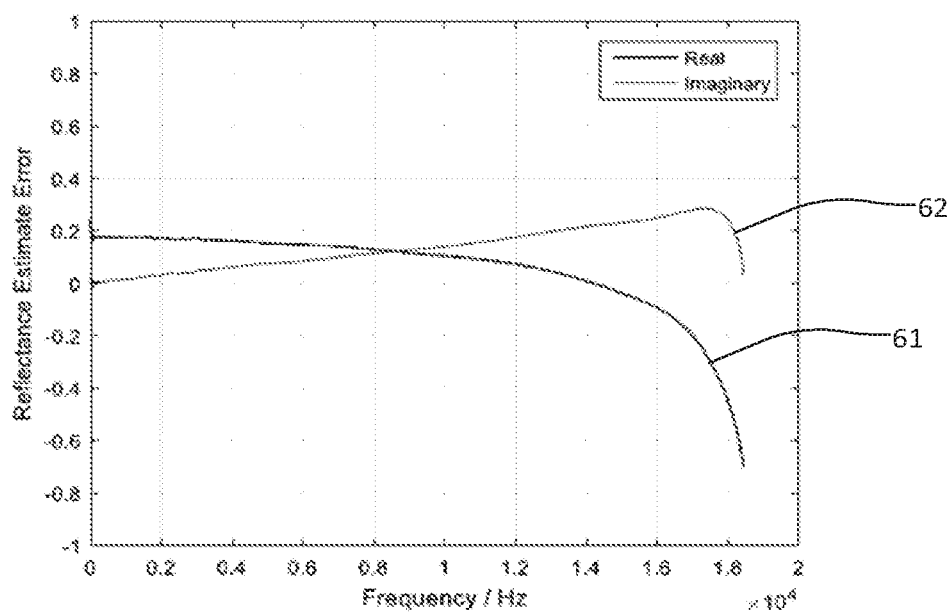
FIG. 9 shows the reflectance estimation error, where the first error is present in the time-domain reflectance measure of FIG. 8.

The introduction of errors related to evanescent modes is clearly seen to affect the TDR 60, shown in FIG. 8, where at least three irregularities 63, 64, 65 in the TDR are seen. FIG. 9 illustrates the effect of evanescent modes on the real part of the reflectance estimation 61 and the imaginary part of the reflectance estimation error 62. It is apparent that the effect is an introduction of non-causality into the reflectance shown in FIG. 9 and that the error is apparent from a frequency proportional error in the estimate of the imaginary part and a somewhat more complicated frequency relationship with the estimate of the real part 61 as seen in FIG. 9.

Figure 13:
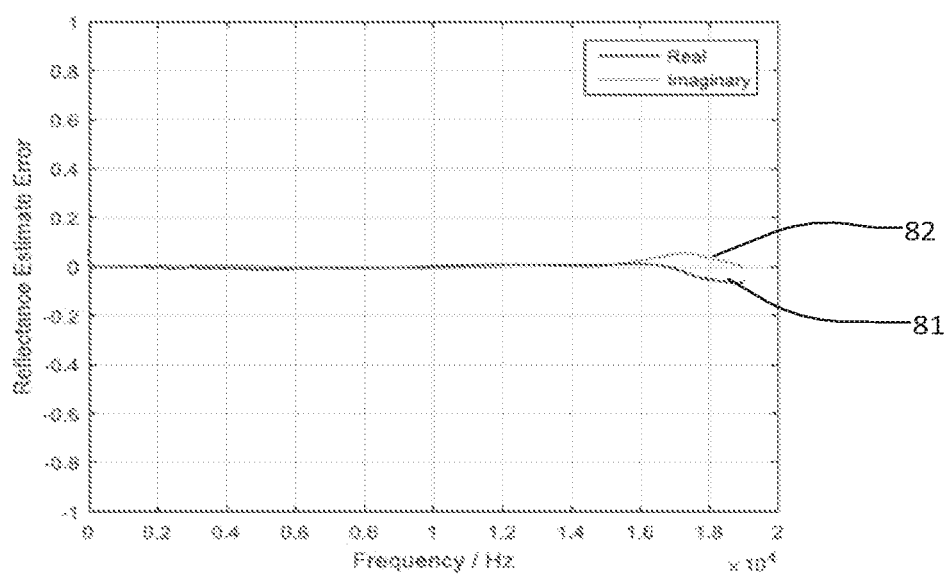
FIG. 13 shows the reflectance estimation according to the compensation achieved in FIG. 12.

From the method described herein, an evanescent-modes compensation parameter is substantially found at least implicit and applied to the measured impedance in an attempt to reduce the error in the estimate of the imaginary part of the reflectance estimation error Im $\varepsilon_R$, obtaining the results as in FIG. 13. Specifically, if a positive error is present in the estimate of the imaginary part of the reflectance estimation error Im $\varepsilon_R$, an increasingly negative mass is subtracted from the measured impedance to minimise the error and vice versa. It is clear that causality is completely restored in reflectance, both in the time and frequency domain. There is a tiny irregularity in the TDR just after t=0 that overlaps slightly below, however this is solely due to a signal processing artefact from windowing. This irregularity is presumably a result of inserting the probe using a mushroom-shaped, rubber ear tip that provides a slight excess volume behind the plane of the probe tip. There is a slight deviation in the errors towards higher frequencies, possibly due to the incapability of perfectly restoring continuity in the reflectance spectrum by adjusting the Nyquist frequency, but also due to the waveguide-like behaviour of a possible misplacement of the probe tip relative to the input plane that the simple addition of an acoustic mass cannot compensate. This is circumvented by simply leaving out higher frequencies in the minimisation of the error.

Figure 10:
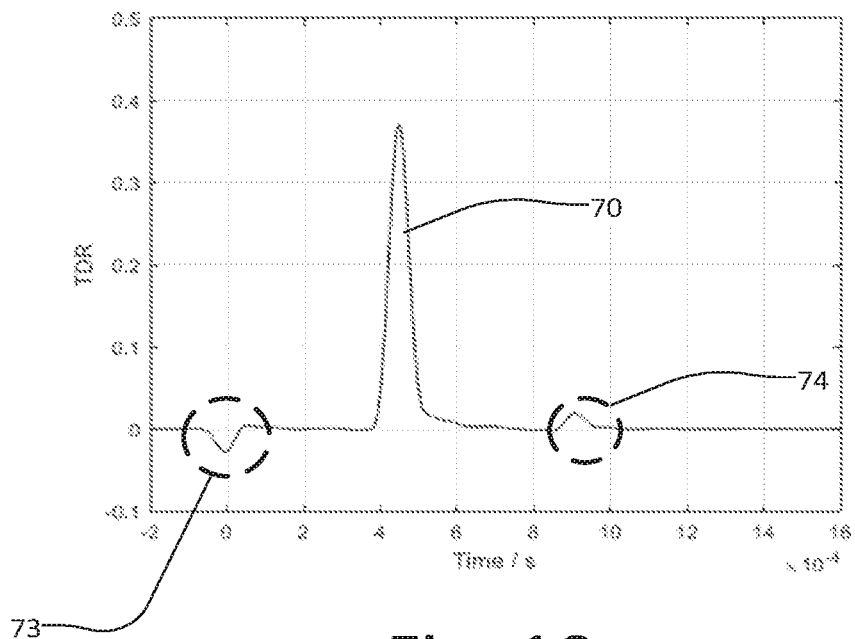
FIG. 10 shows a real time-domain reflectance measure of a waveguide according to an embodiment of the disclosure where a second error is present.
Figure 11:
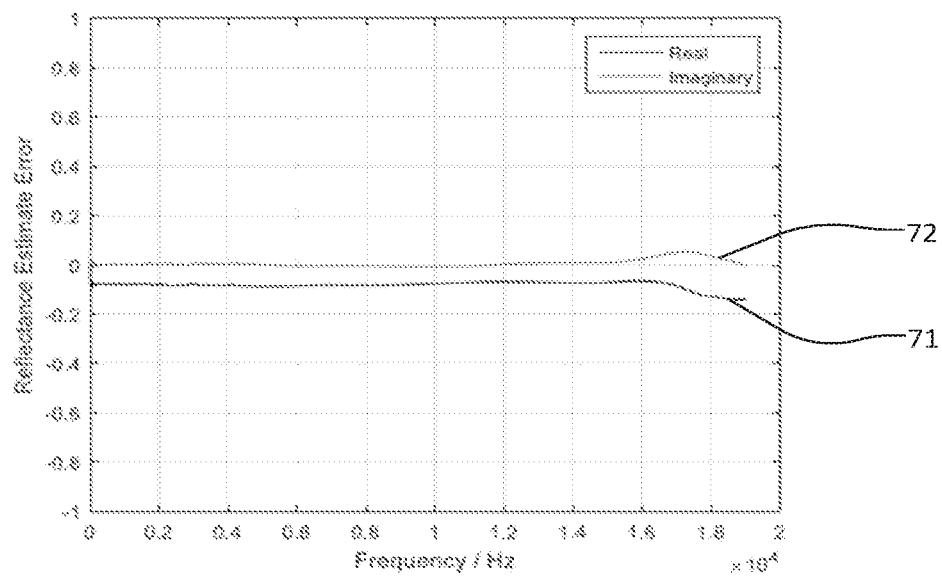
FIG. 11 shows the reflectance estimation error, where the second error arising in the real time-domain reflectance measure according to FIG. 10, is illustrated.

If using the results from a compensation related to evanescent modes, but applying an incorrect characteristic impedance corresponding to a waveguide of Ø0.75 cm the resulting TDR 70 is as illustrated in FIG. 10. Again, it is seen from FIG. 10, that an error caused by an incorrect characteristic impedance introduces irregularities 73, 74 in the TDR 70. In FIGS. 4 and 8, an additional irregularity was mentioned and it should be noted that the irregularity is similarly present in the TDR shown in FIG. 10. However, this error is small and is therefore not clear from FIG. 10, The errors in the real 71 and imaginary part 72 introduced in the TDR is seen from FIG. 11. From FIG. 11, the analytical finding that the characteristic impedance mismatch is only affecting the error in the estimate of the real part of the reflectance is confirmed. Applying the method described herein to especially minimize the real part of the reflectance estimation error, it is apparent that causality of the reflectance measure (R) may be restored.

Accordingly, it is facilitated that an iterative method for adjusting the contributions from evanescent modes and characteristic impedance mismatches separately and/or at the same time, preferably beginning with the evanescent mode compensation since the characteristic impedance mismatch only affects the real part. Thus, causality in the reflectance measure is restored and in effect provides more accurate in-situ measurements of an acoustic load. Specifically, for the characteristic impedance, if the error is negative, the diameter of the waveguide used for calculating characteristic impedance is increased and vice versa.

Figure 12:
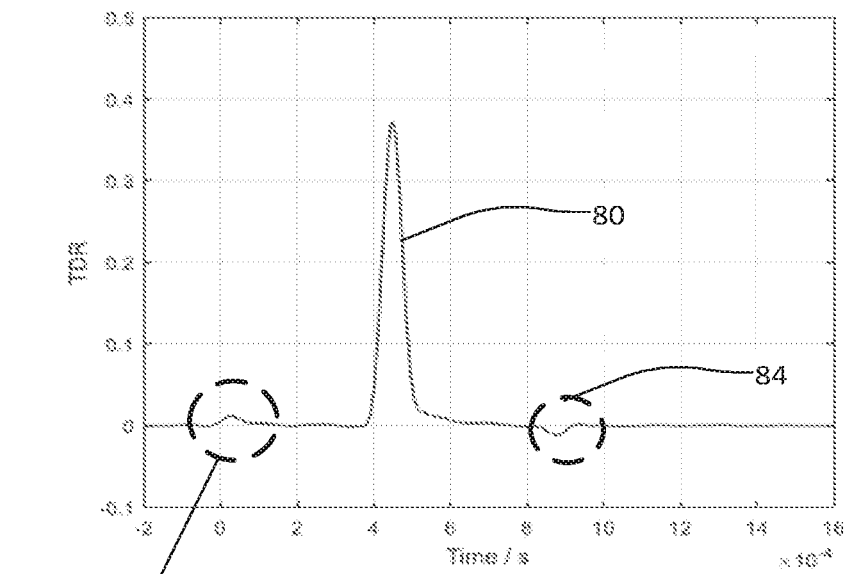

Accordingly, FIGS. 12 and 13 demonstrate the effect of compensating evanescent modes and applying a correct characteristic impedance, found by minimizing the real part of the reflectance estimation error Re $\varepsilon_R$ and the imaginary part of the reflectance estimation error Im $\varepsilon_R$ in a real acoustic waveguide measurement. The compensation parameter $C_1(\omega)$ compensating the characteristic impedance is obtained by adjusting the error in the estimate of the real part of the impedance, i.e., minimizing the error. Similarly, the compensation parameter compensating for evanescent modes is obtained by minimizing the error in at least the imaginary part of the reflectance error estimate. It is apparent from the frequency domain and time domain illustrated in FIGS. 12 and 13, that causality has been completely restored in the reflectance 80 of FIG. 12, by using the method according to claim 1. The small irregularities 83, 84 in the TDR do not represent a non-causal phenomenon, but rather a consequence of the probe not being inserted in a plane, but using an ear tip. In this case, the mushroom-shaped ear tip contributes with a small circular volume behind the tip of the probe, and this causes a small positive reflection. From FIG. 13 it is clearly seen that the minimization of the error estimates of the real 81 and imaginary part 82 through the applied method as described herein has restored causality of the reflectance, removing the contributions to TDR 80 arising due to evanescent modes and a mismatch in characteristic impedance.

As a consequence of using the method described herein, the compensation scheme provided to compensate for errors introduced in in-situ measurements of acoustic waveguides, such as an ear canal may also be used for calculation of an equivalent plane-wave sound pressure recorded by the probe microphone. Thus, when having calculated/measured the equivalent plane wave impedance, the compensation factors to the impedance also facilitates the calculation of the equivalent plane-wave sound pressure by:

$$P(\omega) = P_{meas}(\omega) \frac{Z(\omega)}{Z_{meas}(\omega)} \qquad (9)$$

where $P_m(\omega)$ is the sound pressure recorded by the probe and potentially affected by evanescent modes, $Z_m(\omega)$ is the uncompensated impedance and $Z(\omega)$ is the evanescent-modes compensated impedance. This compensation has potential use in all measurement modalities where sound pressure is to be measured in the ear canal as a foundation to estimating the sound pressure at different positions in the ear canal, e.g., using the forwards-pressure level calibration method or transmission-line models.

Further embodiments of the invention include the following embodiments:

An embodiment, where the method for estimating one or more compensation parameters from impedance measurements of an acoustic load, said method comprising the steps of:
  positioning a probe assembly in an acoustic load, said acoustic load having a first and a second end;
  generating an electrical input signal to an acoustic source within said probe assembly, when said probe assembly is positioned in said first end of said acoustic load to produce an acoustic stimulus in response to said acoustic said electrical input signal;
  measuring an acoustic reflected signal with an acoustic energy detector within said probe assembly;
  estimating based on said measured acoustic reflected signal one or more compensation parameters describing the characteristics of said acoustic load and/or a coupling between the probe and acoustic load, wherein said acoustic reflected signal is given as a measure of a first acoustic impedance, and wherein said estimation step comprises the further step of
  calculating said one or more compensation parameters from said first acoustic impedance and a second characteristic impedance of said acoustic load, whereby said compensation parameters are found by a minimization of one or more error estimates related to said first acoustic impedance and said second characteristic impedance.

An embodiment, wherein the calculation step further comprises the step of:
  estimating a measure of reflectance from said acoustic impedance and said characteristic impedance,
  separating said estimated reflectance and/or acoustic impedance into a first real part and a second imaginary part;
  calculating said one or more compensation parameters from said first real and second imaginary parts.

An embodiment, wherein an initial compensation factor is added to said measured first acoustic impedance prior to the step of calculating said one or more compensation parameters and/or an initial value for said characteristic impedance is used as an input in said calculation step.

An embodiment, wherein, said initial compensation factor is an estimate of an evanescent mode error causing errors in the measured first acoustic impedance.

An embodiment, wherein the calculation step further comprises the step of:
  establishing a relationship between said first real and second imaginary part from a Hilbert transform;
  calculating said one or more error estimates of the real part of said measure of reflectance and/or acoustic impedance from the imaginary part of the measure of reflectance and/or acoustic impedance and/or of the imaginary part of the measure of reflectance and/or acoustic impedance from the real part of the measure of reflectance and/or acoustic impedance using said Hilbert transform;
  minimizing said one or more error estimates in an iterative process until causality is achieved.

An embodiment, wherein said minimization provides a first error estimate of the first real part of reflectance and/or acoustic impedance from the second imaginary part using the Hilbert transform, said first error estimate characterizing a first compensation parameter describing primarily an error related to a characteristic impedance mismatch of said acoustic load in relation to the calculation of reflectance.

An embodiment, wherein said minimization provides a second error estimate of the second imaginary part of reflectance and/or acoustic impedance from the first real part using the Hilbert transform, said second error estimate characterizing a second compensation parameter describing primarily an error related to evanescent modes arising from the coupling between said probe assembly to said load.

An embodiment, wherein the estimation further comprises the step of iteratively estimating a combined set of said one or more compensation parameters from said one or more error estimates.

An embodiment, wherein an iterative and combined estimation of said one or more compensation parameters includes minimizing the second error related to said evanescent modes and the first error related to characteristic impedance mismatch of the acoustic load in relation to calculation of reflectance at the same time.

An embodiment, wherein said compensation parameter found from said minimization of said second error estimate comprises an update parameter, said update parameter intended to update said initial compensation factor, by being added to the detected acoustic reflected signal in order to account for evanescent modes and/or wherein said compensation parameter found from said minimization of said first error estimate comprises an update parameter, said update parameter intended to update said initial value for said characteristic impedance used for calculating said reflectance.

An embodiment, wherein said initial compensation factor is given as an acoustic mass added to said measured first acoustic impedance.

An embodiment, wherein the acoustic load is a waveguide, a musical instrument, an acoustic muffler, a human ear canal or any other acoustical load for which an acoustic impedance is of interest.

In an embodiment, the acoustic impedance measurement system for measuring acoustic impedance of an acoustic application, said measurement system comprising
- a probe assembly configured to be positioned in an acoustic load, said acoustic load having a first and a second end;
- a signal generating unit, generating an electrical input signal to an acoustic source within said probe assembly when said probe assembly is positioned in said first end of said acoustic load to produce an acoustic stimulus in response to said acoustic said electrical input signal;
- a signal measuring unit, measuring an acoustic reflected signal with an acoustic energy detector within said probe assembly;
- a calculation unit said calculation unit being configured to estimate based on said detected acoustic reflected signal one or more compensation parameters describing the characteristics of said acoustic load, wherein said acoustic reflected signal is given as a measure of a first acoustic impedance and wherein said estimation is based on said calculation unit being configured to calculate said one or more compensation parameters from said first acoustic impedance and a second characteristic impedance of said acoustic load, wherein said one or more compensation parameters are found by a minimization of one or more error estimates related to said first acoustic impedance and said second characteristic impedance.

An embodiment, wherein said calculation unit takes as input at least said measured first acoustic impedance and an initial compensation factor, compensating for evanescent modes, wherein said initial compensation factor are added to said first acoustic impedance.

An embodiment, wherein said calculation unit is configured perform said method of the previously described embodiments according to the disclosure, in order to calculate a first error estimate and/or a second error estimate, said first error estimate characterizing a compensation parameter related to a characteristic impedance mismatch between said acoustic load characteristic impedance used for calculating reflectance and said second error estimate characterizing a compensation parameter related to errors caused by evanescent modes resulting from the coupling between probe assembly and load.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e., to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A method to compensate for a first error arising in an impedance measure of an acoustic load due to evanescent modes causing inaccuracies in a reflectance measure of said acoustic load and a second error arising in said reflectance measure due to said acoustic load having an unknown characteristic impedance ($Z_0$), said method comprising the steps of:
   positioning a probe assembly in said acoustic load, said probe assembly comprising a speaker and a microphone, and said acoustic load having a first open end and a second at least partly closed end, wherein a distance between said first open end and said second at least partly closed end defines a length of said acoustic load;
   generating from said speaker an acoustic output signal emitted into said acoustic load from said first open end and configured to propagate along said length of said acoustic load,
   recording with said microphone of said acoustic probe an input signal caused by an incident part and a reflected part of said output signal propagating along said acoustic load, said incident part of said output signal comprising a plane wave part and an evanescent mode part, the method furthermore comprising the steps of i) calculating an acoustic impedance ($Z_m$) based on a relation between said input signal and said output signal, wherein said acoustic impedance ($Z_m$) includes said first error due to said evanescent mode part of said incident part, which first error are given as an approximation using an acoustic mass (L);

ii) setting a starting value ($Z_0'$) of said unknown characteristic impedance ($Z_0$) of said acoustic load;

iii) calculating said reflectance measure (R) from a relationship between said measured acoustic impedance ($Z_m$) and said starting value ($Z_0'$) of said unknown characteristic impedance ($Z_0$);

iv) calculating a reflectance estimation error ($\varepsilon_R$) from a Hilbert transform of an imaginary part of said reflectance measure (R) subtracted from a real part of said reflectance measure (R) and added to a unit imaginary number (I) multiplied by an inverse Hilbert transform of said real part of said reflectance measure (R) subtracted from said unit imaginary number (I) multiplied by an imaginary part of said reflectance measure (R);

v) calculating a real part of said reflectance estimation error ($\varepsilon_R$) and an imaginary part of said reflectance estimation error ($\varepsilon_R$);

vi) adjusting said acoustic mass (L) iteratively until said imaginary part of said reflectance estimation error ($\varepsilon_R$) is minimized, thereby providing said first error arising in said reflectance measure due to said evanescent modes.

2. Method according to claim 1, wherein the method furthermore comprises the step of:

adjusting said starting value ($Z_0'$) of said unknown characteristic impedance ($Z_0$) iteratively until said real part of said reflectance estimation error ($\varepsilon_R$) is minimized, thereby determining said unknown characteristic impedance ($Z_0$) accounting for said second error arising in said reflectance measure due to said starting value ($Z_0'$) of said unknown characteristic impedance ($Z_0$) of said acoustic load.

3. Method according to claim 1, wherein said step of adjusting said acoustic mass (L) iteratively, comprises the iterative steps of subtracting said acoustic mass (L) from said acoustic impedance measure ($Z_m$) and updating said reflectance measure and said imaginary part of said reflectance estimation error until said imaginary part of said reflectance measure is minimized.

4. Method according to claim 1, wherein said steps of adjusting said starting value ($Z_0'$) of said unknown characteristic impedance ($Z_0$) and said step adjusting said acoustic mass (L) accounts for a non-causality contained within said impedance measure due to said evanescent modes and said unknown characteristic impedance.

5. Method according to claim 1, wherein the reflectance estimation error ($\varepsilon_R$) is transformed into any other quantity representing said non-causality contained within said reflectance measure (R) due to said evanescent modes and said unknown characteristic impedance.

6. Method according to claim 1, wherein said acoustic load is a waveguide, a musical instrument, an acoustic muffler, a human ear canal, or any other acoustical load for which said reflectance measure and or said acoustic impedance measure are of interest.

7. Method according to claim 6, wherein said starting value ($Z_0'$) for said characteristic acoustic impedance is provided as an average characteristic impedance of human ear canals, when applying said method to perform reflectance measures of said human ear canal having an unknown characteristic impedance ($Z_0$).

8. Method according to claim 2, wherein said steps of adjusting said starting value ($Z_0'$) of said unknown characteristic impedance ($Z_0$) and said step adjusting said acoustic mass (L) accounts for a non-causality contained within said impedance measure due to said evanescent modes and said unknown characteristic impedance.

9. Method according to claim 3, wherein said steps of adjusting said starting value ($Z_0'$) of said unknown characteristic impedance ($Z_0$) and said step adjusting said acoustic mass (L) accounts for a non-causality contained within said impedance measure due to said evanescent modes and said unknown characteristic impedance.

10. Method according to claim 2, wherein the reflectance estimation error ($\varepsilon_R$) is transformed into any other quantity representing said non-causality contained within said reflectance measure (R) due to said evanescent modes and said unknown characteristic impedance.

11. Method according to claim 3, wherein the reflectance estimation error ($\varepsilon_R$) is transformed into any other quantity representing said non-causality contained within said reflectance measure (R) due to said evanescent modes and said unknown characteristic impedance.

12. Method according to claim 4, wherein the reflectance estimation error ($\varepsilon_R$) is transformed into any other quantity representing said non-causality contained within said reflectance measure (R) due to said evanescent modes and said unknown characteristic impedance.

13. Method according to claim 2, wherein said acoustic load is a waveguide, a musical instrument, an acoustic muffler, a human ear canal or any other acoustical load for which said reflectance measure and or said acoustic impedance measure are of interest.

14. Method according to claim 3, wherein said acoustic load is a waveguide, a musical instrument, an acoustic muffler, a human ear canal or any other acoustical load for which said reflectance measure and or said acoustic impedance measure are of interest.

15. Method according to claim 4, wherein said acoustic load is a waveguide, a musical instrument, an acoustic muffler, a human ear canal or any other acoustical load for which said reflectance measure and or said acoustic impedance measure are of interest.

16. Method according to claim 5, wherein said acoustic load is a waveguide, a musical instrument, an acoustic muffler, a human ear canal or any other acoustical load for which said reflectance measure and or said acoustic impedance measure are of interest.

17. A measurement system configured to output a reflectance measure (R) of an acoustic load, said measurement system comprising a probe assembly configured to be arranged in an acoustic load, said probe assembly having a speaker and a microphone, and said acoustic load having a first open end and a second at least partly closed end, wherein a distance between said first open end and said second at least partly closed end defines a length of said acoustic load; and a signal generating unit, generating from said speaker an output signal emitted into said acoustic load from said first open end and configured to propagate along said length of said acoustic load, wherein said microphone of said acoustic probe is configured to record an input signal caused by an incident part and a reflected part of said output signal propagating along said acoustic load, said system furthermore comprising a calculation unit configured to perform the method steps i) to vi) according to claim 1.

18. Measurement system according to claim 17, wherein said calculation unit takes as input at least said recorded input signal caused by said output signal being reflected from said at least partly closed end of said acoustic load for calculating said acoustic impedance ($Z_m$) including an acoustic mass due to said evanescent modes according to step i), and a starting value of at least one of an acoustic mass (L) and/or said unknown characteristic impedance ($Z_0$) according to step ii).

19. Measurement system according to claim 17, wherein said calculation unit outputs
a reflectance measure (R) including said first error arising from said evanescent modes and said second error arising due to said unknown characteristic impedance ($Z_0$) and
calculates a real part and an imaginary part of said reflectance estimation error ($\varepsilon_R$) according to step v),
wherein said calculation unit upon performing said adjusting step vi) is configured to output a corrected reflectance measure (R) wherein said first error arising due to evanescent modes and said second error arising due to an unknown characteristic impedance of said acoustic load are compensated for.

20. Measurement system according to claim 18, wherein said calculation unit outputs a reflectance measure (R) including said first error arising from said evanescent modes and said second error arising due to said unknown characteristic impedance ($Z_0$) and calculates a real part and an imaginary part of said reflectance estimation error ($\varepsilon_R$) according to step v),
wherein said calculation unit upon performing said adjusting step vi) is configured to output a corrected reflectance measure (R) wherein said first error arising due to evanescent modes and said second error arising due to an unknown characteristic impedance of said acoustic load are compensated for.

* * * * *